United States Patent
Haider et al.

(10) Patent No.: US 11,389,777 B2
(45) Date of Patent: Jul. 19, 2022

(54) OVERALL ENERGY OPTIMIZATION OF BUTANE DEHYDROGENATION TECHNOLOGY BY EFFICIENT REACTOR DESIGN

(71) Applicant: SABIC Global Technologies B.V., Bergen op Zoom (NL)

(72) Inventors: Muhammad H. Haider, Riyadh (SA); Shehzada Khurram, Riyadh (SA); Abdulaziz Al-Zahrani, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/283,167

(22) PCT Filed: Aug. 27, 2019

(86) PCT No.: PCT/IB2019/057214
§ 371 (c)(1),
(2) Date: Apr. 6, 2021

(87) PCT Pub. No.: WO2020/089705
PCT Pub. Date: May 7, 2020

(65) Prior Publication Data
US 2021/0346857 A1    Nov. 11, 2021

Related U.S. Application Data

(60) Provisional application No. 62/755,267, filed on Nov. 2, 2018.

(51) Int. Cl.
*B01J 8/04*     (2006.01)
*B01J 12/00*    (2006.01)
(Continued)

(52) U.S. Cl.
CPC ........... *B01J 8/0465* (2013.01); *B01J 8/0496* (2013.01); *B01J 12/007* (2013.01); *C07C 5/2568* (2013.01);
(Continued)

(58) Field of Classification Search
CPC ...... B01J 8/0465; B01J 8/0496; B01J 12/007; B01J 2208/00203; B01J 2208/00504;
(Continued)

(56) References Cited

U.S. PATENT DOCUMENTS

| | | |
|---|---|---|
| 4,558,168 A | 12/1985 | Gussow et al. |
| 4,962,266 A | 10/1990 | Shum |

(Continued)

FOREIGN PATENT DOCUMENTS

| | | |
|---|---|---|
| EP | 0042537 A1 | 12/1981 |
| WO | WO2017118884 A1 | 7/2017 |

OTHER PUBLICATIONS

Barbieri et al. ("Dehydroisomerization Reaction in a Membrane Reactor: Thermodynamic Analysis", Chemical Engineering Transactions, vol. 23, 2013) (Year: 2013).*

(Continued)

*Primary Examiner* — Ali Z Fadhel
(74) *Attorney, Agent, or Firm* — Norton Rose Fulbright US LLP

(57) ABSTRACT

Reactors and methods of using the reactors to produce 1-butene are disclosed. A feed stream comprising n-butane is flowed to a dehydrogenation compartment of a reactor. The dehydrogenation compartment includes a dehydrogenation catalyst for catalyzing the dehydrogenation of n-butane to produce a dehydrogenation compartment effluent comprising 1-butene, 2-butene, isobutene, and/or unreacted n-butane. The dehydrogenation compartment effluent is flowed to a isomerization compartment of the reactor. The (Continued)

isomerization compartment contains a catalyst for isomerizing 2-butene in the dehydrogenation compartment effluent to produce 1-butene. A heating section is disposed between the dehydrogenation compartment and the isomerization compartment to provide heat for the reactions in both compartments.

20 Claims, 2 Drawing Sheets

(51) Int. Cl.
*C07C 5/25* (2006.01)
*C07C 5/333* (2006.01)
*C07B 35/08* (2006.01)

(52) U.S. Cl.
CPC ... *C07C 5/3337* (2013.01); *B01J 2208/00203* (2013.01); *B01J 2208/00504* (2013.01); *B01J 2208/00539* (2013.01); *B01J 2208/00548* (2013.01); *B01J 2231/52* (2013.01); *C07B 35/08* (2013.01); *C07C 2523/42* (2013.01); *C07C 2523/62* (2013.01); *C07C 2531/10* (2013.01)

(58) Field of Classification Search
CPC .... B01J 2208/00539; B01J 2208/00548; B01J 2231/52; C07C 5/3337; C07C 2523/42; C07C 2523/62; C07C 2531/10; C07C 5/23–2593; C07C 5/32–3337; C07C 5/373; C07B 35/08
See application file for complete search history.

(56) References Cited

U.S. PATENT DOCUMENTS

| | | | |
|---|---|---|---|
| 5,880,324 A | 3/1999 | de Agudelo et al. | |
| 7,485,761 B2 | 2/2009 | Schindler et al. | |
| 9,193,647 B2 | 11/2015 | Giesa et al. | |
| 2004/0247498 A1* | 12/2004 | Phillips | B01J 8/0492 422/600 |
| 2008/0107589 A1 | 5/2008 | von Blucher et al. | |
| 2013/0072738 A1 | 3/2013 | Jung et al. | |
| 2013/0211166 A1 | 8/2013 | Giesa et al. | |
| 2016/0318829 A1* | 11/2016 | Gaertner | C07C 5/48 |

OTHER PUBLICATIONS

"AMBERLYST™ 36DRY Polymeric Catalyst." Product Data Sheet, Dupont, Jun. 2019, 2 pages.

International Search Report and Written Opinion from PCT/IB2019/057214 dated Dec. 16, 2019, 12 pages.

Jeon et al., "Selective Synthesis of Butene-1 Through Double-bond Migration of Butene-2 over η-Alumina Catalysts" *Bull. Korean Chem. Soc.*, 2014, 35(9):2669.

Kikuchi et al. "Effect of Sn Addition on n-Butane Dehydrogenation over Alumina-supported Pt Catalysts Prepared by Co-impregnation and Sol-gel Methods." *J. Jpn. Petrol. Inst.*, 55, 3 (2012) 206-213.

Pavlov et al. "Processes of Synthesis of 1-Butene from 2-Butene by the Positional Isomerization on Sulfocation Exchangers." *Russ. J. App. Chem*, 82, 6 (2009) 1117-1122.

* cited by examiner

OVERALL ENERGY OPTIMIZATION OF BUTANE DEHYDROGENATION TECHNOLOGY BY EFFICIENT REACTOR DESIGN

CROSS REFERENCE TO RELATED APPLICATIONS

This application is a national phase application under 35 U.S.C. § 371 of International Application No. PCT/IB2019/057214 filed Aug. 27, 2019, which claims priority to U.S. Provisional Patent Application No. 62/755,267 filed Nov. 2, 2018. The entire contents of each of the above-referenced disclosures is specifically incorporated by reference herein without disclaimer.

FIELD OF INVENTION

The present invention generally relates to reactors and methods for producing 1-butene. More specifically, the present invention relates to reactors and methods for producing 1-butene from n-butane via dehydrogenation followed by isomerization.

BACKGROUND OF THE INVENTION 1-butene is commonly used as co-monomer for producing certain types of polyethylene (e.g., linear low density polyethylene). 1-butene is also used as an effective monomer for producing high octane fuels. Furthermore, 1-butene is used as a precursor in many chemical production processes including polypropylene resin, butylene oxide, and butanone.

Conventionally, 1-butene is produced by separating crude $C_4$ streams obtained in refinery or chemical production processes. However, the crude $C_4$ streams generally contain both 1-butene and 2-butene in addition to other $C_4$ hydrocarbons. The overall concentration of 1-butene in the crude $C_4$ streams is generally low. Additionally, the separation of 1-butene and 2-butene requires a large amount of energy, resulting in high production cost for 1-butene. Another method for producing 1-butene includes dimerization of ethylene. However, this method requires organometallic catalysts and complicated operational steps. Therefore, the production cost for 1-butene using ethylene dimerization is high. Dehydrogenation of n-butane can be used for producing 1-butene. This method produces a mixture of $C_4$ hydrocarbons including both 1-butene, 2-butene, and isobutene. Thus, a large amount of energy is required for purification of 1-butene.

Overall, while systems and methods of producing 1-butene exist, the need for improvements in this field persists in light of at least the aforementioned drawbacks for the conventional methods.

BRIEF SUMMARY OF THE INVENTION

A solution to at least some of the above-mentioned problems associated with the production systems and processes for 1-butene has been discovered. The solution resides in a reactor and a method of using the reactor to produce 1-butene. The reactor includes a dehydrogenation compartment and an isomerization compartment with a heating section disposed there between. N-butane can be dehydrogenated in the dehydrogenation compartment to produce 1-butene, 2-butene, and/or isobutylene. The effluent from the dehydrogenation compartment is further processed in the isomerization compartment to convert substantially all the 2-butene into 1-butene. This can be beneficial for eliminating the need for the downstream separation of 1-butene and 2-butene, resulting in reduced energy cost for producing 1-butene. Notably, this method performs the dehydrogenation and isomerization in a single reactor, resulting in simplified operational processes. Additionally, the dehydrogenation compartment and the isomerization compartment share the same heating section, which can further reduce the production cost for 1-butene compared to conventional methods.

Embodiments of the invention include a reactor for dehydrogenating n-butane to produce 1-butene. The reactor comprises a dehydrogenation compartment comprising a dehydrogenation catalyst adapted to catalyze dehydrogenation of n-butane and an isomerization compartment comprising a sulfocation exchanger catalyst adapted to catalyze isomerization of 2-butene to 1-butene.

Embodiments of the invention include a reactor for dehydrogenating n-butane to produce 1-butene. The reactor comprises a dehydrogenation compartment comprising a dehydrogenation catalyst adapted to catalyze dehydrogenation of n-butane and an isomerization compartment comprising a sulfocation exchanger catalyst adapted to catalyze isomerization of 2-butene to 1-butene. The reactor further comprises a channel for flowing effluent from the dehydrogenation compartment into the isomerization compartment. The reactor further still comprises a heating section disposed between the dehydrogenation compartment and the isomerization compartment.

Embodiments of the invention include a method of dehydrogenating n-butane to produce 1-butene. The method comprises flowing n-butane into a dehydrogenation compartment of a reactor. The dehydrogenation compartment comprises a dehydrogenation catalyst adapted to catalyze dehydrogenation of the n-butane. The method further comprises subjecting the n-butane to reaction conditions in the dehydrogenation compartment sufficient to dehydrogenate the n-butane to produce at least 1-butene and 2-butene. The method further comprises flowing a dehydrogenation compartment effluent comprising 1-butene and 2-butene into an isomerization compartment of the reactor. The isomerization compartment comprises a sulfocation exchanger catalyst adapted to catalyze isomerization of 2-butene to 1-butene. The method further still comprises subjecting the dehydrogenation compartment effluent to reaction conditions, in the isomerization compartment, sufficient to isomerize at least some of the 2-butene of the dehydrogenation compartment effluent to form 1-butene.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Figure 1A:
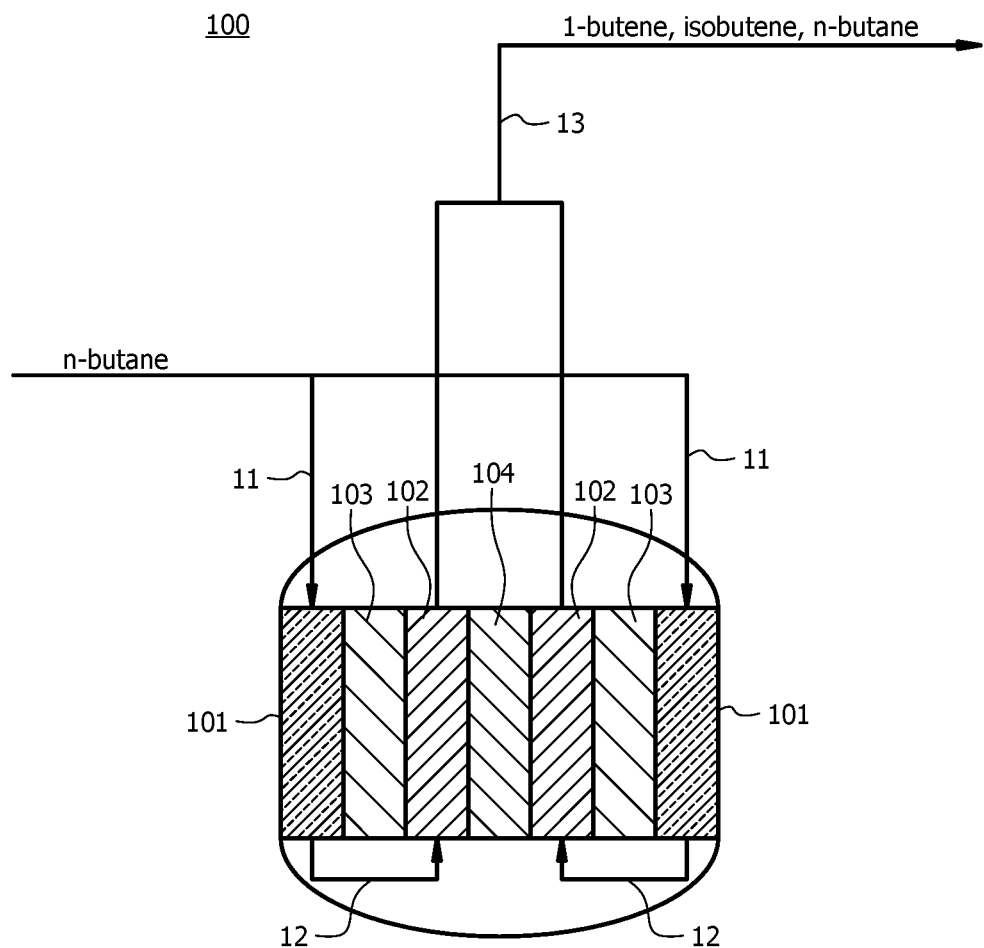
FIG. 1A shows a front sectional view of a reactor for producing 1-butene using n-butane, according to embodiments of the invention.

Currently, 1-butene can be produced by directly separating 1-butene from $C_4$ mixtures produced in a refinery and/or chemical production process (e.g., steam cracking). Additionally, 1-butene can be produced via dimerization of ethylene in the presence of organometallic catalysts. Furthermore, dehydrogenation of n-butane can also be used for 1-butene production. However, for all these conventional methods, downstream separation of 1-butene from 2-butene is energy intensive, resulting in high production costs for 1-butene. The present invention provides a solution to the problem. The solution is premised on a reactor and a method of using the reactor to produce 1-butene. The reactor comprises a dehydrogenation compartment connected to an isomerization compartment via a channel such that dehydrogenation of n-butene and isomerization of 2-butene can be carried out in a single reactor. This method is capable of substantially eliminating the need to separate 1-butene and 2-butene, thereby reducing the energy cost without overcomplicating the operating process for producing 1-butene. These and other non-limiting aspects of the present invention are discussed in further detail in the following sections.

A. Reactor for Producing 1-Butene

In embodiments of the invention, the reactor for producing 1-butene can include an integrated dehydrogenation compartment and isomerization compartment. With reference to FIG. 1, a schematic diagram is shown of reactor 100 that is capable of producing 1-butene with reduced production cost compared to conventional systems for 1-butene production. According to embodiments of the invention, reactor 100 comprises dehydrogenation compartment 101. Dehydrogenation compartment 101 may contain a dehydrogenation catalyst adapted to catalyze dehydrogenation of n-butane. In embodiments of the invention, reactor 100 includes a feed inlet configured to receive feed stream 11 comprising n-butane into dehydrogenation compartment 101.

In embodiments of the invention, the dehydrogenation catalyst in dehydrogenation compartment 101 includes platinum, tin, or combinations thereof. The dehydrogenation catalyst may be supported on a support material comprising alumina, silica, or combinations thereof. In embodiments of the invention, a dehydrogenation catalyst (metal) to support material ratio in dehydrogenation compartment 101 may be in a range of 0.1 to 20 and all ranges and values there between including ranges of 0.1 to 0.2, 0.2 to 0.3, 0.3 to 0.4, 0.4 to 0.5, 0.5 to 0.6, 0.6 to 0.7, 0.7 to 0.8, 0.8 to 0.9, 0.9 to 1.0, 1.0 to 2.0, 2.0 to 3.0, 3.0 to 4.0, 4.0 to 5.0, 5.0 to 6.0, 6.0 to 7.0, 7.0 to 8.0, 8.0 to 9.0, 9.0 to 10.0, 10.0 to 11.0, 11.0 to 12.0, 12.0 to 13.0, 13.0 to 14.0, 14.0 to 15.0, 15.0 to 16.0, 16.0 to 17.0, 17.0 to 18.0, 18.0 to 19.0, and 19.0 to 20.0. According to embodiments of the invention, the dehydrogenation catalyst and the support material may be included in a fixed catalyst bed disposed in dehydrogenation compartment 101. The dehydrogenation catalyst may have a surface area of 100 to 200 $m^2/m^3$ and all ranges and values there between including ranges of 100 to 110 $m^2/m^3$, 110 to 120 $m^2/m^3$, 120 to 130 $m^2/m^3$, 130 to 140 $m^2/m^3$, 140 to 150 $m^2/m^3$, 150 to 160 $m^2/m^3$, 160 to 170 $m^2/m^3$, 170 to 180 $m^2/m^3$, 180 to 190 $m^2/m^3$, 190 to 200 $m^2/m^3$.

According to embodiments of the invention, reactor 100 further comprises isomerization compartment 102. Isomerization compartment 102 may contain a sulfocation exchanger catalyst adapted to catalyze isomerization of 2-butene to 1-butene. In embodiments of the invention, the sulfocation exchanger catalyst includes styrene and divinylbenzene, or combinations thereof. In embodiments of the invention, the sulfocation exchanger catalyst may include an ion exchange resin, copolymer of styrene and divinylbenzene, or combinations thereof. In embodiment of the invention, reactor 100 may comprise a channel in fluid communication with an outlet of dehydrogenation compartment 101 and an inlet of isomerization compartment 102 such that dehydrogenation compartment effluent stream 12 flows from dehydrogenation compartment 101 to isomerization compartment 102. According to embodiments of the invention, the outlet of dehydrogenation compartment 101 may be disposed at the bottom thereof. The inlet of isomerization compartment 102 may be disposed at the bottom thereof.

According to embodiments of the invention, reactor 100 further comprises heating section 103 disposed between dehydrogenation compartment 101 and isomerization compartment 102. In embodiments of the invention, heating section 103 is adapted to provide heat for both dehydrogenation of n-butane in dehydrogenation compartment 101 and isomerization of 2-butene in isomerization compartment 102. Heating section 103 may comprise heating coils, gas burners, or combinations thereof.

Figure 1B:
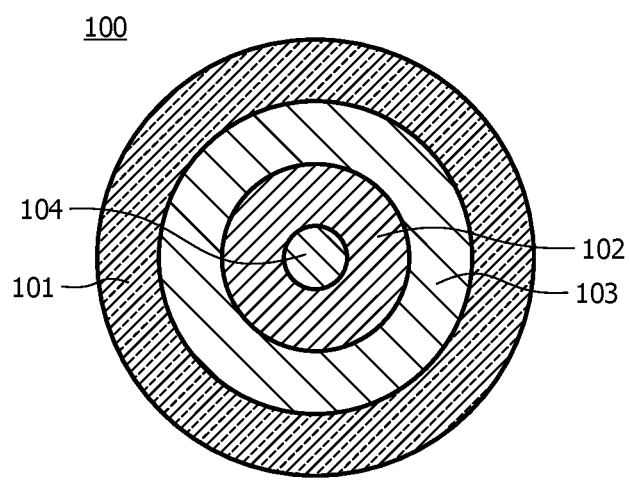
FIG. 1B shows a top sectional view of a reactor for producing 1-butene using n-butane, according to embodiments of the invention.

In embodiments of the invention, reactor 100 includes an outlet adapted to release isomerization compartment effluent stream 13 from isomerization compartment 102. In embodiments of the invention, reactor 100 includes a housing adapted to contain dehydrogenation compartment 101, isomerization compartment 102, and heating section 103. According to embodiments of the invention, reactor 100 may have a cylindrical shape and dehydrogenation compartment 101, isomerization compartment 102, heating section 103 each individually comprise an annular shaped column, as shown in FIG. 1A and FIG. 1B. In embodiments of the invention, the annular shaped columns of dehydrogenation compartment 101, isomerization compartment 102, and heating section 103 may form a substantially concentric, multilayered structure. As shown in FIG. 1B, considering from the circumference to the center of the multilayered structure, dehydrogenation compartment 101 may be disposed as the outermost layer, heating section 103 may be disposed as the second outermost layer, and isomerization compartment 102 as the third layer. In embodiments of the invention, second heating section 104 may be disposed in the center of the multilayered structure of reactor 100. It should be noted that embodiments of the invention can include reactor 100 having a cross sectional surface in other shapes, including but not limited to rectangular, polygon, elliptical, triangle, or any irregular shape. In embodiments of the invention, reactor 100 may comprise other configurations. For instance, reactor 100 may have a configuration with isomerization compartment 102 as the outermost compartment of reactor 100, heating section 103 as the second section from the outermost compartment, and dehydrogenation compartment as the third compartment from the outermost of reactor 100.

B. Method of Producing 1-Butene

Figure 2:
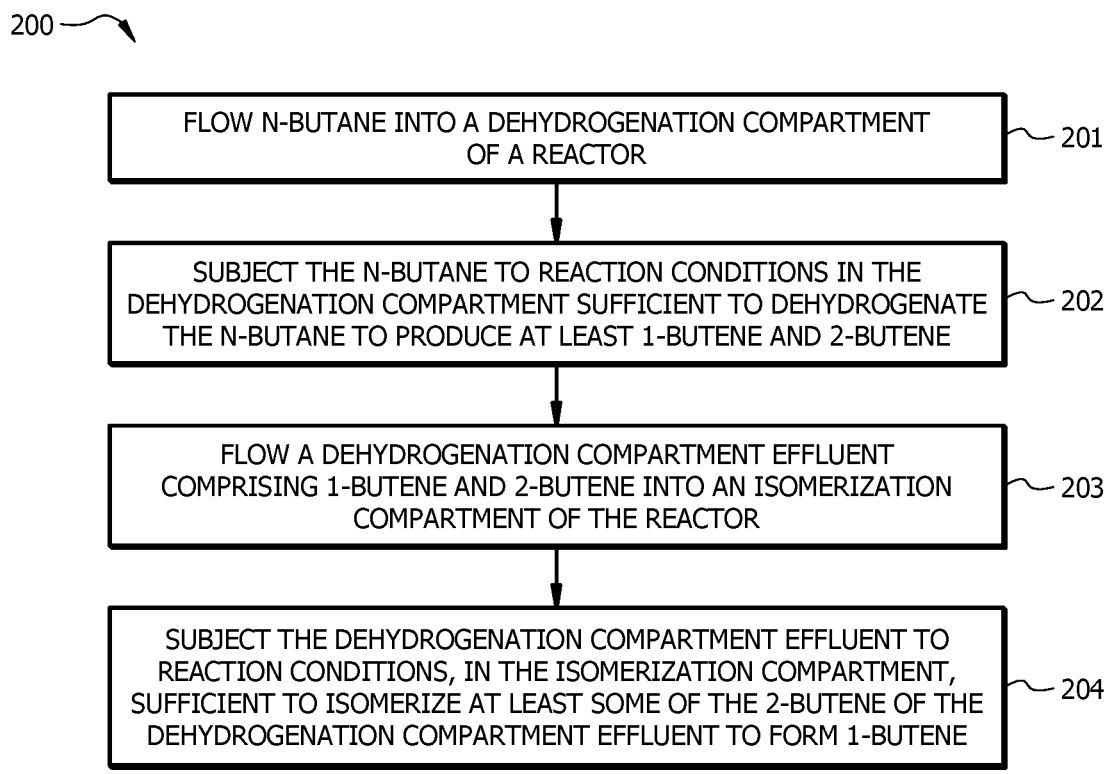
FIG. 2 shows a schematic flowchart of a method of producing 1-butene using n-butane, according to embodiments of the invention.

Methods of producing 1-butene have been discovered. The methods may be capable of reducing the energy cost for producing 1-butene compared to conventional methods. As shown in FIG. 2, embodiments of the invention include method 200 for producing 1-butene. Method 200 may be implemented by reactor 100, as shown in FIGS. 1A and/or 1B. According to embodiments of the invention, as shown in block 201, method 200 may include flowing feed stream 11 comprising n-butane into dehydrogenation compartment 101 of reactor 100. In embodiment of the invention, feed stream 11 may be preheated to a temperature of 100 to 150° C. prior to flowing at block 201 and all ranges and values there between including ranges 100 to 105° C., 105 to 110° C., 110 to 115° C., 115 to 120° C., 120 to 125° C., 125 to 130° C., 130 to 135° C., 135 to 140° C., 140 to 145° C., 145 to 150° C. Dehydrogenation compartment 101 may comprise a fixed catalyst bed including Pt, Sn, or combinations thereof.

According to embodiments of the invention, as shown in block 202, method 200 further comprises subjecting the n-butane of feed stream 11 to reaction conditions in dehydrogenation compartment 101 sufficient to dehydrogenate the n-butane to produce 1-butene and 2-butene. The subjecting step at block 202 may further produce isobutene. In embodiments of the invention, the reaction conditions in dehydrogenation compartment 101 at block 202 includes a reaction temperature of 400 to 550° C. and all ranges and values there between including ranges 400 to 410° C., 410 to 420° C., 420 to 430° C., 430 to 440° C., 440 to 450° C., 450 to 460° C., 460 to 470° C., 470 to 480° C., 480 to 490° C., 490 to 500° C., 500 to 510° C., 510 to 520° C., 520 to 530° C., 530 to 540° C., 540 to 550° C. The reaction conditions at block 202 may further include reaction pressure in dehydrogenation compartment in a range of 0 to 5 bar and all ranges and values there between including 0 to 0.5 bar, 0.5 to 1.0 bar, 1.0 to 1.5 bar, 1.5 to 2.0 bar, 2.0 to 2.5 bar, 2.5 to 3.0 bar, 3.0 to 3.5 bar, 3.5 to 4.0 bar, 4.0 to 4.5 bar, and 4.5 to 5.0 bar. The reaction conditions at block 202 may further include a weight hourly space velocity of 1000 to 5000 $hr^{-1}$ and all ranges and values there between 1000 to 1500 $hr^{-1}$, 1500 to 2000 $hr^{-1}$, 2000 to 2500 $hr^{-1}$, 2500 to 3000 $hr^{-1}$, 3000 to 3500 $hr^{-1}$, 3500 to 4000 $hr^{-1}$, 4000 to 4500 $hr^{-1}$, and 4500 to 5000 $hr^{-1}$. In embodiments of the invention, at block 202, n-butane is converted in dehydrogenation compartment 101 at a conversion ratio of 35 to 55% and all ranges and values there between including ranges 35 to 36%, 36 to 37%, 37 to 38%, 38 to 39%, 39 to 40%, 40 to 41%, 41 to 42%, 42 to 43%, 43 to 44%, 44 to 45%, 45 to 46%, 46 to 47%, 47 to 48%, 48 to 49%, 49 to 50%, 50 to 51%, 51 to 52%, 52 to 53%, 53 to 54%, and 54 to 55%.

According to embodiments of the invention, as shown in block 203, method 200 further includes flowing dehydrogenation compartment effluent stream 12 into isomerization compartment 102 of reactor 100. In embodiments of the invention, isomerization compartment 102 may comprise sulfocation exchanger catalyst including styrene, divinylbenzene, or combinations thereof. As shown in block 204, method 200 may include, in isomerization compartment 102, subjecting dehydrogenation compartment effluent stream 12 to reaction conditions sufficient to isomerize 2-butene of dehydrogenation compartment effluent stream 12 to form 1-butene in isomerization compartment effluent stream 13. In embodiments of the invention, the reaction conditions in isomerization compartment 102 at block 204 includes a reaction temperature of 400 to 500° C. and all ranges and values there between including ranges of 400 to 405° C., 405 to 410° C., 410 to 415° C., 415 to 420° C., 420 to 425° C., 425 to 430° C., 430 to 435° C., 435 to 440° C., 440 to 445° C., 445 to 450° C., 450 to 455° C., 455 to 460° C., 460 to 465° C., 465 to 470° C., 470 to 475° C., 475 to 480° C., 480 to 485° C., 485 to 490° C., 490 to 495° C., 495 to 500° C. The reaction conditions at block 204 may further include a reaction temperature in a range of 0 to 5 bar and all ranges and values there between including 0 to 0.5 bar, 0.5 to 1.0 bar, 1.0 to 1.5 bar, 1.5 to 2.0 bar, 2.0 to 2.5 bar, 2.5 to 3.0 bar, 3.0 to 3.5 bar, 3.5 to 4.0 bar, 4.0 to 4.5 bar, and 4.5 to 5.0 bar. The reaction conditions at block 204 may further still include weight hourly space velocity in a range of 1000 to 5000 $hr^{-1}$ and all ranges and values there between 1000 to 1500 $hr^{-1}$, 1500 to 2000 $hr^{-1}$, 2000 to 2500 $hr^{-1}$, 2500 to 3000 hr$^{-1}$, 3000 to 3500 hr$^{-1}$, 3500 to 4000 hr$^{-1}$, 4000 to 4500 hr$^{-1}$, and 4500 to 5000 hr$^{-1}$.

In embodiments of the invention, substantially all of 2-butene of dehydrogenation compartment effluent stream 12 is converted to 1-butene at block 204. Isomerization compartment effluent stream 13 may further comprise isobutene and/or unreacted n-butane. In embodiments of the invention, isomerization compartment effluent stream 13 may comprise 80 to 95 wt. % 1-butene and all ranges and values there between including 80 to 81 wt. %, 81 to 82 wt. %, 82 to 83 wt. %, 83 to 84 wt. %, 84 to 85 wt. %, 85 to 86 wt. %, 86 to 87 wt. %, 87 to 88 wt. %, 88 to 89 wt. %, 89 to 90 wt. %, 90 to 91 wt. %, 91 to 92 wt. %, 92 to 93 wt. %, 93 to 94 wt. %, and 94 to 95 wt. %. Isomerization compartment effluent stream 13 may comprise 5 to 20 wt. % isobutene and 45 to 65 wt. % unreacted n-butane. According to embodiments of the invention, isomerization compartment effluent stream 13 can be separated by a separation unit to produce purified 1-butene.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

In the context of the present invention, at least the following 17 embodiments are described. Embodiment 1 is a reactor for dehydrogenating n-butane to produce 1-butene. The reactor includes a dehydrogenation compartment containing a dehydrogenation catalyst adapted to catalyze dehydrogenation of n-butane, and an isomerization compartment containing a sulfocation exchanger catalyst adapted to catalyze isomerization of 2-butene to 1-butene. Embodiment 1 is the reactor of embodiment 1, further including a channel for flowing effluent from the dehydrogenation compartment into the isomerization compartment. Embodiment 3 is the reactor of either of embodiments 1 or 2, further including a heating section disposed between the dehydrogenation compartment and the isomerization compartment. Embodiment 4 is the reactor of embodiment 3, wherein the heating section comprises gas burners or heating coils, or combinations thereof. Embodiment 5 is the reactor of either of embodiments 3 or 4, wherein the dehydrogenation compartment, the isomerization compartment, and the heating section each individually contain an annular column, wherein the annular columns of the dehydrogenation compartment, the isomerization compartment, and the heating section are substantially concentric. Embodiment 6 is the reactor of any of embodiments 1 to 5, wherein the dehydrogenation catalyst is selected from the group consisting of platinum, and/or tin. Embodiment 7 is the reactor of embodiment 6, wherein the dehydrogenation catalyst is supported on a supporting material selected from the group consisting of alumina and silica. Embodiment 8 is the reactor of embodiment 7, wherein the dehydrogenation compartment contains one or more fixed catalyst bed comprising the dehydrogenation catalyst and the supporting material. Embodiment 9 is the reactor of any of embodiments 1 to 8, wherein the sulfocation exchanger catalyst is selected from the group consisting of styrene, divinylbenzene, or combinations thereof.

Embodiment 10 is a method of dehydrogenating n-butane to produce 1-butene. The method includes flowing n-butane into the dehydrogenation compartment of the reactor of any of embodiments 1 to 9. The method further includes subjecting the n-butane to reaction conditions in the dehydrogenation compartment sufficient to dehydrogenate the n-butane to produce at least 1-butene and 2-butene. The method also includes flowing a dehydrogenation compartment effluent comprising 1-butene and 2-butene into the isomerization compartment of the reactor. The method additionally includes subjecting the dehydrogenation compartment effluent to reaction conditions, in the isomerizing compartment, sufficient to isomerize at least some of the 2-butene of the dehydrogenation compartment effluent to form 1-butene. Embodiment 11 is a method of dehydrogenating n-butane to produce 1-butene. The method includes flowing n-butane into a dehydrogenation compartment of a reactor, the dehydrogenation compartment containing a dehydrogenation catalyst adapted to catalyze dehydrogenation of the n-butane. The method also includes subjecting the n-butane to reaction conditions in the dehydrogenation compartment sufficient to dehydrogenate the n-butane to produce at least 1-butene and 2-butene. The method further includes flowing a dehydrogenation compartment effluent comprising 1-butene and 2-butene into an isomerization compartment of the reactor, the isomerization compartment containing a sulfocation exchanger catalyst adapted to catalyze isomerization of 2-butene to 1-butene. The method additionally includes subjecting the dehydrogenation compartment effluent to reaction conditions, in the isomerizing compartment, sufficient to isomerize at least some of the 2-butene of the dehydrogenation compartment effluent to form 1-butene. Embodiment 12 is the method of either of embodiments 10 or 11, wherein the reaction conditions in the dehydrogenation compartment include a reaction temperature of 400 to 550° C. and a reaction pressure of 0 to 5 bar. Embodiment 13 is the method of any of embodiments 10 to 12, wherein the reaction conditions in the dehydrogenation compartment include a weight hourly space velocity of 1000 to 5000 hr$^{-1}$. Embodiment 14 is the method of any of embodiments 10 to 13, wherein dehydrogenation compartment effluent further contains n-butane and/or isobutene. Embodiment 15 is the method of any of embodiments 10 to 14, wherein the reaction conditions in the isomerization compartment include a reaction temperature of 400 to 500° C. and a reaction pressure of 0 to 1 bar. Embodiment 16 is the method of any of embodiments 10 to 15, wherein the reaction conditions in the isomerization compartment include a weight hourly space velocity of 1000 to 5000 hr$^{-1}$. Embodiment 17 is the method of any of embodiments 10 to 16, wherein the effluent from the isomerization compartment contains n-butane, 1-butene, isobutene, or combinations thereof.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A reactor for dehydrogenating n-butane to produce 1-butene, the reactor comprising:
   a dehydrogenation compartment comprising a dehydrogenation catalyst adapted to catalyze dehydrogenation of n-butane, and
   an isomerization compartment comprising a sulfocation exchanger catalyst adapted to catalyze isomerization of 2-butene to 1-butene.

2. The reactor of claim 1, further comprising a channel for flowing effluent from the dehydrogenation compartment into the isomerization compartment.

3. The reactor of claim 1, further comprising a heating section disposed between the dehydrogenation compartment and the isomerization compartment.

4. The reactor of claim 3, wherein the heating section comprises gas burners or heating coils, or combinations thereof.

5. The reactor of claim 3, wherein the dehydrogenation compartment, the isomerization compartment, and the heating section each individually comprise an annular column, wherein the annular columns of the dehydrogenation compartment, the isomerization compartment, and the heating section are substantially concentric.

6. The reactor of claim 1, wherein the dehydrogenation catalyst is selected from the group consisting of platinum, and/or tin.

7. The reactor of claim 6, wherein the dehydrogenation catalyst is supported on a supporting material selected from the group consisting of alumina and silica.

8. The reactor of claim 7, wherein the dehydrogenation compartment contains one or more fixed catalyst bed comprising the dehydrogenation catalyst and the supporting material.

9. The reactor of claim 1, wherein the sulfocation exchanger catalyst is selected from the group consisting of styrene, divinylbenzene, or combinations thereof.

10. A method of dehydrogenating n-butane to produce 1-butene, the method comprising:
    flowing n-butane into the dehydrogenation compartment of the reactor of claim 1;
    subjecting the n-butane to reaction conditions in the dehydrogenation compartment sufficient to dehydrogenate the n-butane to produce at least 1-butene and 2-butene;
    flowing a dehydrogenation compartment effluent comprising 1-butene and 2-butene into the isomerization compartment of the reactor; and
    subjecting the dehydrogenation compartment effluent to reaction conditions, in the isomerizing compartment, sufficient to isomerize at least some of the 2-butene of the dehydrogenation compartment effluent to form 1-butene.

11. The method of claim 10, wherein the reaction conditions in the dehydrogenation compartment comprise a reaction temperature of 400 to 550° C. and a reaction pressure of 0 to 5 bar.

12. The method of claim 11, wherein the effluent from the isomerization compartment comprises n-butane, 1-butene, isobutene, or combinations thereof.

13. The method of claim 10, wherein the reaction conditions in the dehydrogenation compartment comprise a weight hourly space velocity of 1000 to 5000 $hr^{-1}$.

14. The method of claim 13, wherein the effluent from the isomerization compartment comprises n-butane, 1-butene, isobutene, or combinations thereof.

15. The method of claim 10, wherein dehydrogenation compartment effluent further comprises n-butane and/or isobutene.

16. The method of claim 10, wherein the reaction conditions in the isomerization compartment comprise a reaction temperature of 400 to 500° C. and a reaction pressure of 0 to 1 bar.

17. The method of claim 10, wherein the reaction conditions in the isomerization compartment comprise a weight hourly space velocity of 1000 to 5000 $hr^{-1}$.

18. The method of claim 10, wherein the effluent from the isomerization compartment comprises n-butane, 1-butene, isobutene, or combinations thereof.

19. A method of dehydrogenating n-butane to produce 1-butene, the method comprising:
    flowing n-butane into a dehydrogenation compartment of a reactor, the dehydrogenation compartment comprising a dehydrogenation catalyst adapted to catalyze dehydrogenation of the n-butane,
    subjecting the n-butane to reaction conditions in the dehydrogenation compartment sufficient to dehydrogenate the n-butane to produce at least 1-butene and 2-butene;
    flowing a dehydrogenation compartment effluent comprising 1-butene and 2-butene into an isomerization compartment of the reactor, the isomerization compartment comprising a sulfocation exchanger catalyst adapted to catalyze isomerization of 2-butene to 1-butene; and
    subjecting the dehydrogenation compartment effluent to reaction conditions, in the isomerizing compartment, sufficient to isomerize at least some of the 2-butene of the dehydrogenation compartment effluent to form 1-butene.

20. The method of claim 19, wherein the effluent from the isomerization compartment comprises n-butane, 1-butene, isobutene, or combinations thereof.

* * * * *